(12) United States Patent
Keren et al.

(10) Patent No.: US 8,235,933 B2
(45) Date of Patent: Aug. 7, 2012

(54) METHODS AND APPARATUS FOR REDUCING LOCALIZED CIRCULATORY SYSTEM PRESSURE

(75) Inventors: Gad Keren, Qrxat-Ono (IL); Randy Kesten, Mountain View, CA (US)

(73) Assignee: V-Wave Ltd., Hod-Hasharon (IL)

( * ) Notice: Subject to any disclaimer, the term of this patent is extended or adjusted under 35 U.S.C. 154(b) by 0 days.

(21) Appl. No.: 13/107,832

(22) Filed: May 13, 2011

(65) Prior Publication Data

US 2011/0218477 A1    Sep. 8, 2011

Related U.S. Application Data

(63) Continuation of application No. 09/839,643, filed on Apr. 20, 2001, now Pat. No. 8,091,556.

(51) Int. Cl.
*A61M 5/00*    (2006.01)

(52) U.S. Cl. ............... 604/8; 604/9; 623/3.26; 623/3.28

(58) Field of Classification Search .................. 604/8–9; 623/1.15, 1.18, 1.24–1.26
See application file for complete search history.

(56) References Cited

U.S. PATENT DOCUMENTS

| | | |
|---|---|---|
| 3,874,388 A | 4/1975 | King et al. |
| 4,601,309 A | 7/1986 | Chang |
| 4,662,355 A | 5/1987 | Pieronne et al. |
| 4,705,507 A | 11/1987 | Boyles |
| 4,979,955 A | 12/1990 | Smith |
| 4,995,857 A | 2/1991 | Arnold |
| 5,186,431 A | 2/1993 | Tamari |
| 5,267,940 A | 12/1993 | Moulder |
| 5,290,227 A | 3/1994 | Pasque |
| 5,326,374 A | 7/1994 | Ilbawi et al. |
| 5,332,402 A | 7/1994 | Teitelbaum |
| 5,334,217 A | 8/1994 | Das |
| 5,409,019 A | 4/1995 | Wilk |
| 5,429,144 A | 7/1995 | Wilk |
| 5,500,015 A | 3/1996 | Deac |
| 5,556,386 A | 9/1996 | Todd |
| 5,584,803 A | 12/1996 | Stevens et al. |
| 5,597,377 A | 1/1997 | Aldea |
| 5,655,548 A | 8/1997 | Nelson et al. |
| 5,662,711 A | 9/1997 | Douglas |
| 5,725,552 A | 3/1998 | Kotula et al. |
| 5,795,307 A | 8/1998 | Krueger |
| 5,824,071 A | 10/1998 | Nelson et al. |

(Continued)

FOREIGN PATENT DOCUMENTS

FR    2 827 153    1/2003

(Continued)

OTHER PUBLICATIONS

U.S. Appl. No. 13/107,843, filed May 13, 2011, Keren et al.

(Continued)

*Primary Examiner* — Patricia Bianco
*Assistant Examiner* — Camtu Nguyen
(74) *Attorney, Agent, or Firm* — Jones Day; Nicola A. Pisano; Jaime D. Choi

(57) ABSTRACT

The present invention is directed to methods and apparatus for decreasing pressure in the left atrium of a patient by implanting a valved shunt through the atrial septum, whereby a volume of blood sufficient to reduce pressure in said left atrium is released to the right atrium.

10 Claims, 4 Drawing Sheets

U.S. PATENT DOCUMENTS

| | | | |
|---|---|---|---|
| 5,916,193 | A | 6/1999 | Stevens et al. |
| 5,957,949 | A | 9/1999 | Leonhardt et al. |
| 6,039,759 | A | 3/2000 | Carpentier et al. |
| 6,126,686 | A | 10/2000 | Badylak et al. |
| 6,165,188 | A | 12/2000 | Saadat et al. |
| 6,210,318 | B1 | 4/2001 | Lederman |
| 6,217,541 | B1 | 4/2001 | Yu |
| 6,254,564 | B1 | 7/2001 | Wilk et al. |
| 6,270,526 | B1 | 8/2001 | Cox |
| 6,277,078 | B1 | 8/2001 | Porat et al. |
| 6,302,892 | B1 | 10/2001 | Wilk |
| 6,344,022 | B1 | 2/2002 | Jarvik |
| 6,358,277 | B1 | 3/2002 | Duran |
| 6,447,539 | B1 | 9/2002 | Nelson et al. |
| 6,458,153 | B1 | 10/2002 | Bailey et al. |
| 6,468,303 | B1 | 10/2002 | Amplatz et al. |
| 6,527,698 | B1 | 3/2003 | Kung et al. |
| 6,544,208 | B2 | 4/2003 | Ethier et al. |
| 6,562,066 | B1 | 5/2003 | Martin |
| 6,572,652 | B2 | 6/2003 | Shaknovich |
| 6,589,198 | B1 | 7/2003 | Soltanpour et al. |
| 6,632,169 | B2 | 10/2003 | Korakianitis et al. |
| 6,638,303 | B1 | 10/2003 | Campbell |
| 6,641,610 | B2 | 11/2003 | Wolf et al. |
| 7,001,409 | B2 | 2/2006 | Amplatz |
| 7,294,115 | B1 | 11/2007 | Wilk |
| 2002/0165606 | A1* | 11/2002 | Wolf et al. ............ 623/1.24 |
| 2002/0173742 | A1 | 11/2002 | Keren et al. |
| 2003/0100920 | A1 | 5/2003 | Akin et al. |
| 2003/0125798 | A1 | 7/2003 | Martin |
| 2003/0216679 | A1 | 11/2003 | Wolf et al. |
| 2004/0010219 | A1 | 1/2004 | McCusker et al. |
| 2004/0077988 | A1 | 4/2004 | Tweden et al. |
| 2004/0088045 | A1 | 5/2004 | Cox |
| 2004/0093075 | A1 | 5/2004 | Kuehne |
| 2004/0147869 | A1 | 7/2004 | Wolf et al. |
| 2004/0147871 | A1 | 7/2004 | Burnett |
| 2004/0162514 | A1 | 8/2004 | Alferness et al. |
| 2004/0210190 | A1 | 10/2004 | Kohler et al. |
| 2004/0210307 | A1 | 10/2004 | Khairkhahan |
| 2005/0033351 | A1 | 2/2005 | Newton |
| 2005/0148925 | A1 | 7/2005 | Rottenberg et al. |
| 2005/0165344 | A1 | 7/2005 | Dobak, III |
| 2006/0116710 | A1 | 6/2006 | Corcoran et al. |
| 2006/0122647 | A1 | 6/2006 | Callaghan et al. |
| 2006/0167541 | A1 | 7/2006 | Lattouf |
| 2007/0010852 | A1 | 1/2007 | Blaeser et al. |
| 2007/0282157 | A1 | 12/2007 | Rottenberg et al. |
| 2007/0299384 | A1 | 12/2007 | Faul et al. |
| 2008/0262602 | A1 | 10/2008 | Wilk et al. |

FOREIGN PATENT DOCUMENTS

| | | |
|---|---|---|
| WO | WO 99/60941 | 12/1999 |
| WO | WO 2005/027752 A1 | 3/2005 |
| WO | WO 2005/074367 | 8/2005 |

OTHER PUBLICATIONS

U.S. Appl. No. 13/108,698, filed May 16, 2011, Rottenberg et al.
U.S. Appl. No. 13/108,672, filed May 16, 2011, Rottenberg et al.
U.S. Appl. No. 13/108,850, filed May 16, 2011, Rottenberg et al.
U.S. Appl. No. 13/108,880, filed May 16, 2011, Nitzan et al.
U.S. Appl. No. 13/193,309, filed Jul. 28, 2011, Nitzan et al.
U.S. Appl. No. 13/193,335, filed Jul. 28, 2011, Nitzan et al.
Ando et al., "Left ventricular decompression through a patent foramen ovale in a patient with hypertrophic cardiomyopathy: A case report," Cardiovascular Ultrasound 2: 1-7 (2004).
Bristow et al, "Improvement in cardiac myocite function by biological effects of medical therapy: A new concept in the treatment of heart failure," European Heart Journal 16(Suppl.F): 20-31 (1995).
Case et al., "Relief of High Left-Atrial Pressure in Left-Ventricular Failure," Lancet, pp. 841-842 (Oct. 17, 1964).
Coats et al., "Controlled trial of physical training in chronic heart failure: Exercise performance, hemodynamics, ventilation, and autonomic function," Circulation 85: 2119-2131 (1992).
Davies et al., "Reduced contraction and altered frequency response of isolated ventricular myocytes from patients with heart failure," Circulation 92: 2540-2549 (1995).
Ennezat et al., "An unusual case of low-flow, low-gradient severe aortic stenosis: Left-to-right shunt due to atrial septal defect," Cardiology 113(2): 146-148 (2009).
Ewert et al., "Acute left heart failure after interventional occlusion of an atrial septal defect," Z Kardiol. 90(5): 362-366 (May 2001).
Ewert et al., "Masked left ventricular restriction in elderly patients with atrial septal defects: A contraindication for closure?" Catheterization and Cardiovascular Interventions 52: 177-180 (2001).
Geiran et al., "Changes in cardiac dynamics by opening an interventricular shunt in dogs," J. Surg. Res. 48(1): 6-12 (Jan. 1990).
Gelernter-Yaniv et al., "Transcatheter closure of left-to-right interatrial shunts to resolve hypoxemia," Congenit. Heart Dis. 31(1): 47-53 (Jan. 2008).
Gewillig et al., "Creation with a stent of an unrestrictive lasting atrial communication," Cardio. Young 12(4): 404-407 (2002).
International Search Report for PCT/IL2005/000131, 3 pages (Apr. 7, 2008).
Kramer et al., "Controlled study of captopril in chronic heart failure: A rest and exercise hemodynamic study," Circulation 67(4): 807-816 (1983).
Lai et al., "Bidirectional shunt through a residual atrial septal defect after percutaneous transvenous mitral commissurotomy," Cardiology 83(3): 205-207 (1993).
Lemmer et al., "Surgical implications of atrial septal defect complicating aortic balloon valvuloplasty," Ann. Thorac. Surg. 48(2): 295-297 (Aug. 1989).
Merriam-Webster "Definition of 'Chamber'," OnLine Dictionary 2004, Abstract.
Schubert et al., "Left ventricular conditioning in the elderly patient to prevent congestive heart failure after transcatheter closure of the atrial septal defect," Catheter Cardiovasc. Interv. 64(3): 333-337 (2005).
Stormer et al., "Comparative study of in vitro flow characteristics between a human aortic valve and a designed aortic valve and six corresponding types of prosthetic heart valves," European Surgical Research 8(2): 117-131 (1976).
Stumper et al., "Modified technique of stent fenestration of the atrial septum," Heart 89: 1227-1230 (2003).
Zhou et al., "Unidirectional valve patch for repair of cardiac septal defects with pulmonary hypertension," Annals of Thoracic Surgeons 60: 1245-1249 (1995).
USPTO Advisory Action for U.S. Appl. No. 10/597,666, 3 pages (Mar. 12, 2010).
USPTO Final Office Action for U.S. Appl. No. 10/597,666, 10 pages (Jan. 7, 2010).
USPTO Non-Final Office Action for U.S. Appl. No. 10/597,666, 10 pages (Mar. 24, 2009).
USPTO Final Office Action for U.S. Appl. No. 10/597,666, 9 pages (Jan. 5, 2009).
USPTO Non-Final Office Action for U.S. Appl. No. 10/597,666, 10 pages (Mar. 28, 2008).
USPTO Non-Final Office Action for U.S. Appl. No. 09/839,643, 11 pages (Jul. 6, 2011).
USPTO Examiner's Answer to Appeal Brief for U.S. Appl. No. 09/839,643, 13 pages (Apr. 14, 2011).
USPTO Non-Final Office Action for U.S. Appl. No. 09/839,643, 10 pages (Sep. 1, 2010).
USPTO Non-Final Office Action for U.S. Appl. No. 09/839,643, 9 pages (Apr. 27, 2010).
USPTO Non-Final Office Action for U.S. Appl. No. 09/839,643, 12 pages (Nov. 12, 2009).
USPTO Advisory Action for U.S. Appl. No. 09/839,643, 3 pages (Sep. 16, 2009).
USPTO Final Office Action for U.S. Appl. No. 09/839,643, 10 pages (Jul. 10, 2009).
USPTO Non-Final Office Action for U.S. Appl. No. 09/839,643, 10 pages (Dec. 16, 2008).
USPTO Final Office Action for U.S. Appl. No. 09/839,643, 8 pages (Mar. 24, 2008).

USPTO Non-Final Office Action for U.S. Appl. No. 09/839,643, 6 pages (Feb. 24, 2006).
USPTO Non-Final Office Action for U.S. Appl. No. 09/839,643, 12 pages (Jun. 27, 2005).
USPTO Advisory Action for U.S. Appl. No. 09/839,643, 3 pages (May 3, 2005).
USPTO Final Office Action for U.S. Appl. No. 09/839,643, 20 pages (Jan. 7, 2005).
USPTO Non-Final Office Action for U.S. Appl. No. 09/839,643, 11 pages (Jul. 29, 2004).
USPTO Final Office Action for U.S. Appl. No. 09/839,643, 9 pages (Jan. 16, 2003).
USPTO Non-Final Office Action for U.S. Appl. No. 09/839,643, 9 pages (Aug. 9, 2002).
USPTO Final Office Action for U.S. Appl. No. 11/048,807, 11 pages (Mar. 4, 2008).
USPTO Non-Final Office Action for U.S. Appl. No. 11/048,807, 10 pages (Jul. 30, 2007).

* cited by examiner

METHODS AND APPARATUS FOR REDUCING LOCALIZED CIRCULATORY SYSTEM PRESSURE

CROSS-REFERENCE TO RELATED APPLICATIONS

This application is a continuation under 35 U.S.C. §120 of U.S. patent application Ser. No. 09/839,643, filed Apr. 20, 2001 now U.S. Pat. No. 8,091,556 and entitled "Methods and Apparatus for Reducing Localized Circulatory System Pressure," the entire contents of which are incorporated herein by reference.

FIELD OF THE INVENTION

The present invention relates to treatments for reducing specific localized points of high pressure within the circulatory system, and more particularly to methods and apparatus to either acutely or chronically reduce left ventricular diastolic pressure that is created as a result of congestive heart failure or similar indications.

BACKGROUND OF THE INVENTION

Congestive heart failure (CHF) is recognized as the most common cause of hospitalization and mortality in Western society. CHF is an extremely serious affliction that has a great impact on the quality of life; it involves the loss of heart rate variability and rate responsive mechanisms in the heart, leading to impaired ventricular relaxation and low exercise tolerance. The disease afflicts about 4 million Americans in any given year; in the USA alone, there are annually about 400,000 new cases, 1 million hospital admissions, and $8 billion cost of care. Congestive heart failure is a syndrome characterized by left ventricular dysfunction, reduced exercise tolerance, impaired quality of life and dramatically shortened life expectancy. Decreased contractility of the left ventricle leads to reduced cardiac output with consequent systemic arterial and venous vasoconstriction. CHF develops generally in the course of months or years, and can be the end stage of chronic hypertension, infarction, angina, or diabetes. Heart failure, however caused, represents an intrinsic property of the muscle, and slow relaxation due to slow intracellular calcium removal by the sarcoplasmic reticulum is an important factor. In the normal, healthy heart the duration of contraction and relaxation decreases with increasing heart rate. This ensures a diastolic period of sufficient duration, which is important (a) for filling of the ventricle, and (b) because coronary perfusion and myocardial oxygen supply occurs only during diastole. The duration of contraction and relaxation is determined by calcium removal from the contractile filaments, mainly by the calcium pump in the sarcoplasmic reticulum Increased heart rate causes more rapid relaxation due to increased activation of the calcium pump. The latter mechanism is impaired in the hypertrophied or failing heart due to reduced transcription of the genes that supply the calcium pump proteins. Therefore, in heart failure patients an increase of heart rate may almost abolish the diastolic interval, which leads to reduced ventricular filling, and reduces myocardial blood supply (Davies et al., 1995, "Reduced Contraction and Altered Frequency Response of Isolated Ventricular Myocytes From Patients With Heart Failure," Circulation 92: 2540-2549).

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure with a resulting difference in pathophysiology of the failing heart, such as the dilatation of the left ventricular chamber. Etiologies that can lead to this form of failure include idiopathic cardiomyopathy, viral cardiomyopathy, and ischemic cardiomyopathy. The process of ventricular dilatation is generally the result of chronic volume overload or specific damage to the myocardium In a normal heart that is exposed to long term increased cardiac output requirements, for example, that of an athlete, there is an adaptive process of ventricular dilation and myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate. The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filing pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Presently available treatments for CHF fall into three generally categories: (1) pharmacological, e.g., diuretics; (2) assist systems, e.g., pumps; and (3) surgical treatments. With respect to pharmacological treatments, diuretics have been used to reduce the workload of the heart by reducing blood volume and preload. While drug treatment improves quality of life, it has little effect on survival. Current pharmacological treatment includes a combination of diuretics, vasodilators, inotropes, .beta.-blockers, and Angiotensin-Converting-Enzy-me (ACE)-inhibitors (Bristow & Gilbert, 1995, "Improvement in Cardiac Myocyte Function by Biological Effects of Medical Therapy: A New Concept in the Treatment of Heart Failure," European Heart Journal 16, Supplement F: 20-31). The effect is a decrease of symptoms, and improved quality of life, but little change in mortality. Moreover, the exercise tolerance of most patients is extremely low, as a consequence of limited oxygen supply through the lungs. Long lasting lack of exercise and malnutrition may contribute to the condition and partly explain the exercise intolerance. Indeed, the lack of exercise and deterioration of cardiac muscle may each contribute to each other, with a snowballing effect (Coats et al., 1992, "Controlled Trial of Physical Training in Chronic Heart Failure: Exercise Performance, Hemodynamics, Ventilation, and Autonomic Function," Circulation 85: 2119-2131). Clinically, preload is defined in several ways including left ventricular end diastolic pressure (LVEDP), or left ventricular end diastolic volume (LVEDV). Physiologically, the preferred definition is the length of stretch of the sarcomere at end diastole. Diuretics reduce extra cellular fluid that builds in congestive heart failure patients increasing preload conditions. Nitrates, arteriolar vasodilators, angiotensin converting enzyme inhibitors have been used to treat heart failure through the reduction of cardiac workload through the reduction of afterload. Afterload may be defined as the tension or stress required in the wall of the ventricle during ejection. Inotropes such as digoxin are cardiac glycosides and function to increase cardiac output by increasing the force and speed of cardiac muscle contraction. These drug therapies offer some beneficial effects but do not stop the progression of the disease. Captopril, enalapril and other inhibitors of angiotensin-converting enzyme (ACE) have been used to treat congestive heart failure. See Merck Index, 1759 and 3521(11th ed. 1989); Kramer, B. L. et al. Circulation 1983, 67(4):755-763. However, such ACE inhibitors have generally provided only moderate or poor results. For example, captopril therapy generally provides only small increases in exercise time and functional capacity. Captopril also has provided only small reductions in mortality rates.

Assist devices used to treat CHF include, for example, mechanical pumps. Mechanical pumps reduce the load on the heart by performing all or part of the pumping function normally done by the heart. Currently, mechanical pumps are used to sustain the patient while a donor heart for transplantation becomes available for the patient. There are also a number of pacing devices used to treat CHF. However, in the chronic ischemic heart, high rate pacing may lead to increased diastolic pressure, indicating calcium overload and damage of the muscle fibers. Finally, there are at least three surgical procedures for treatment of heart failure: 1) heart transplant; 2) dynamic cardiomyoplasty; and 3) the Batista partial left ventriculectomy. Heart transplantation has serious limitations including restricted availability of organs and adverse effects of immunosuppressive therapies required following heart transplantation. Cardiomyoplasty includes wrapping the heart with skeletal muscle and electrically stimulating the muscle to contract synchronously with the heart in order to help the pumping function of the heart. The Batista partial left ventriculectomy includes surgically remodeling the left ventricle by removing a segment of the muscular wall. This procedure reduces the diameter of the dilated heart, which in turn reduces the loading of the heart. However, this extremely invasive procedure reduces muscle mass of the heart.

One category of CHF is diastolic heart failure (DHF), which afflicts between 30% and 70% of those patients with heart failure. DHF is an episodic clinical syndrome that can instigate pulmonary edema, possibly necessitating hospitalization and ventilatory support. The heart is a complex pump structured of two atria and two ventricles that pump blood in parallel into the pulmonary circulation at a relatively low pressure (right ventricle peak systolic pressure is about 25 mmHg) and the systemic circulation (left ventricle peak systolic pressure is about 120 mmHg). During the diastolic phase of the cardiac cycle the ventricles of the heart fill via the respective atria. The pressure differential that propels blood from the respective venous circulations to the atria and ventricles (systemic to the right ventricle and pulmonary to the left ventricle) is low, less than about 5 mmHg. On the left side, during diastole (when the mitral valve opens), pressure in the left atrium normally is not more than 12 mmHg. Due to active diastolic relaxation at the onset of diastole, the pressure difference between the left atrium and the left ventricle is augmented contributing to the early rapid diastolic filling of the left ventricle. Diastolic pressures in the atrium and the ventricle at this phase of the cardiac cycle drop quickly to less than 5 mmHg and equalize. At this point during diastole, the process of filling the left ventricle partially stops (diastasis) and is renewed only towards late diastole, when active contraction of the atrium occurs, resulting in increased left atrial pressure and an increased pressure differential between the atrium and the ventricle. Atrial contraction is very important for maintaining adequate left ventricular filling during exercise and other states of increased cardiac output demand, or when the left ventricle fails to relax normally such as during ischemia or LV hypertrophy. Toward the end of diastole, pressure in the left ventricle (LVEDP) is increased but is normally not more than 12 mmHg.

Disease states in which active and passive relaxation properties of the left ventricle are disturbed, or the pumping and emptying capacity of the ventricle is reduced, may be translated to increased diastolic pressures in the left ventricle. The higher pressures and distension of the left ventricle cause a rise in wall stress and increased oxygen consumption. Up to a limit, the increased diastolic pressure and increased ventricular size result in augmented stroke volume. This compensatory mechanism is limited and has a significant physiologic price mainly when the slope of the pressure-volume curves turn steep, and left ventricular diastolic pressures becomes markedly high (>20 mmHg). At this point, a state of pulmonary congestion may ensue, turning later to a life threatening state of pulmonary edema.

A number of cardiovascular diseases can cause significant cardiac dysfunction and lead to the above-mentioned pathophysiologic state and pulmonary edema. These include: hypertension, ischemic heart disease state and post myocardial infarction, idiopathic dilated cardiomyopathy, valvular heart disease, including aortic stenosis, mitral stenosis, aortic regurgitation, mitral regurgitation, and combined valvular heart disease. Other primary myocardial diseases such as post partum and hypertrophic cardiomyopathy may cause similar conditions. In all these disease states with either decreased ability for the left ventricle to pump blood (systolic dysfunction) or reduced fling capacity (diastolic dysfunction) left ventricular diastolic pressure rises. Increased diastolic pressure in the left ventricle eventually in and of itself becomes a cause for greater degradation in cardiac function than occurred as a result of the original insult. The augmented pressures may cause as stated previously pulmonary congestion and dyspnea. At extreme conditions the clinical state may deteriorate to pulmonary edema.

There are several known techniques to attempt to overcome the state of left ventricular dysfunction, increased diastolic left ventricular pressures and pulmonary congestion. However, none are fully satisfactory. For example, pharmacological treatments are the only practical methods for chronic therapy for most of the population with congestive heart failure. The pharmacological agents used to treat congestive heart failure result in a reduction in diastolic pressure and prevention of pulmonary and peripheral congestion discussed above, i.e., diuretics, vasodilators and digoxin. Diuretics reduce the volume load and thereby reduce preload and diastolic wall stress. Vasodilators have a dual effect in reducing arterial resistance as well as increasing venous capacitance, thereby reducing preload and after load and wall stress throughout the cardiac cycle. These drugs, either direct acting on the vasculature or via neurohormonal mechanisms (ACE inhibitors), are limited in their effect since they may cause hypotension in a significant number of patients with myocardial dysfunction. These pharmacological agents are of limited value mainly because of their side effects. The use of diuretics is associated with side effects related to the drugs and to the detrimental effect on renal function. Vasodilators have also many side effects some of which limit the use of the drugs and their efficacy including hypotension in many patients. Drug therapy results in many of the patients in relative clinical stability. However, episodes where intraventricular diastolic pressure may rise above physiologic needs for cardiac stroke volume augmentation and culminate into pulmonary edema occur often and are very difficult to manage.

In extreme acute situations, temporary assist devices and intraaortic balloons may be helpful. Cardiac transplantation and chronic LVAD implants are solutions available for a small part of the patient population and as last resort. However, all the assist devices currently used are intended to improve pumping capacity of the heart and increase cardiac output to levels compatible with normal life. Finally, cardiac transplantation is another solution, but is not a very practical and is limited to extreme cases and as are the various assist devices. The mechanical devices were built to allow propulsion of significant amount of blood (liters/min) and this is also their main technological limitation. The need for power supply, relatively large pumps and danger of hemolysis and infection are all of significant concern.

Thus, there exists a long-felt and as of yet unsolved need for a treatment that addresses the course of congestive heart failure, and in particular the high pressure of the left ventricle and the compounding factors that are associated with it. It would therefore be desirable to provide methods, apparatus and treatments that beneficially reduce and regulate the pressure within the left ventricle. It is an object of the present invention to provide methods and apparatus for reducing left ventricular end diastolic pressure, and more particularly to provide methods and apparatus without deleterious side effects. It is a further object of the present invention to provide methods and apparatus that can be used in a minimally invasive manner for both acute and chronic treatments.

SUMMARY OF THE INVENTION

The present invention reduces the increased diastolic pressure that can occur as part of the clinical syndrome referred to as Congestive Heart Failure (CHF). Passive and semi-passive devices to reduce left ventricular end-diastolic pressure are disclosed, and in preferred embodiments, a shunt-type device allows a small volume of blood to be released from the left ventricle to reduce the pressure. Certain embodiments use a passive check-valve that allows flow only above a given threshold pressure, while others use a passive check-valve that allows flow only within a window between a lower pressure threshold and a higher-pressure threshold. Embodiments employing check valves prevent shunting during left ventricular systole. Alternatively, semi-passive embodiments have a valve activated by an external signal, such as an intra-corporeal electrical battery or an externally coupled energy source. A third type of preferred embodiment of the invention employs an device such as a pump to actively move blood, with the intent of preventing further deterioration of the patient's heart failure or allowing for some reversal of the heart failure. For example in patients presenting with diastolic heart failure (DHF) the present invention prevents this occurrence by reducing diastolic pressures in the left atrium below the excessive levels that would otherwise have caused pulmonary edema.

The present invention is thus directed to methods and apparatus for decreasing pressure in a first portion of a vessel of the cardiac structure of a patient by implanting a shunt communicating with an area outside said first portion, whereby a volume of blood sufficient to reduce pressure in said first portion is released. Preferably, the first portion comprises the left ventricle and the pressure reduced is the end diastolic pressure, which is accomplished by having the shunt communicate with the left ventricle so a small volume of blood is released from the left ventricle to reduce the end diastolic pressure. Most preferably, the shunt selectively permits flow when a pressure differential between the left ventricle and another chamber of a heart above a threshold pressure, whereby shunting is prevented during left ventricular systole, or, alternatively, selectively permits flow when a pressure differential between the left ventricle and another chamber of a heart is between a lower threshold and a higher threshold, whereby shunting is again prevented during left ventricular systole. In certain embodiments a semi-passive check-valve is controlled and actuated by an external signal, either using a signal generated by an intra-corporeal electrical battery or an externally coupled energy source. In certain embodiments, the shunt has a pump with an input connected to the left ventricle, or other portion with excessive pressure, and an output connected to a volume of lower pressure. The preferred method of implanting the shunt to effect the present invention is by deploying a tubular element having two ends and a tissue affixation element disposed at each of said ends via a catheter, preferably, the fixation element is a shape retaining metallic material that returns to its original shape as part of the retention aspect of its function. In preferred embodiments of the apparatus, the tubular element is comprised of a biologically inert non-metallic material.

DETAILED DESCRIPTION OF THE PREFERRED EMBODIMENTS

Figure 1:
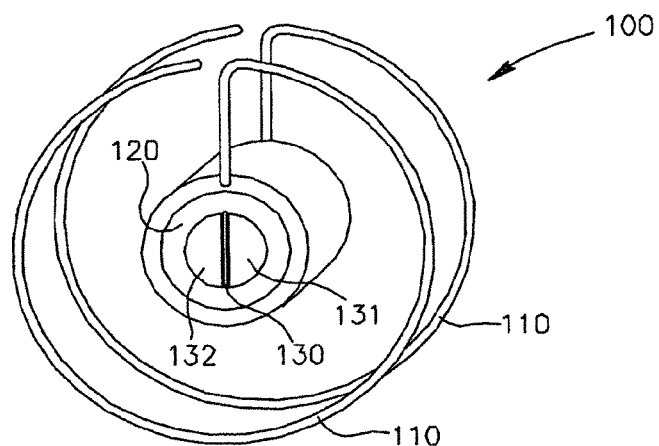
FIG. 1 is a perspective view of a first embodiment of an implantable shunt made in accordance with the present invention.

Referring now to FIG. 1, there is shown a perspective view of a first embodiment of a shunt 100 made in accordance with the present invention. The shunt 100 is comprised of a fixation element 110, which is shown as a planar circular element. It will be understood, however, that the fixation element 110 can be circular, polygonal, spiral or many other shapes. Moreover, the fixation element can lie in a single plane or be curved in multiple planes, such as in a helical configuration. It can be constructed of a variety of materials that offer the elastic range and spring-like characteristics that will enable passage through a catheter lumen, or through the lumen of another implantation assistance device, in a relatively straightened configuration and then recovery of its fill fixation configuration shape. In certain embodiments, the fixation element can be made of reduced size and then expanded through the use of shape-memory alloys (SMA's), such as nickel-titanium (NiTi, also known as nitinol), that change shape in response to temperature changes and which are fabricated such that the temperature change from below body temperature to body temperature causes the shape conversion necessary for implantation. If SMA materials are not used, suitable materials include super-elastic metals, such as NiTi or stainless steel, such as the alloy ELGILOY®, commonly used for medical implants. Additionally, polymeric materials can be used to form the fixation element or as a coating over a metallic core. The fixation element may be coated and/or textured as so as to increase its biocompatibility or to increase the degree to which it quickly becomes endothelialized, which may be desired in some implantation conditions.

As illustrated, the fixation element 110 surrounds and positions the shunt tube element 120, which is provided so as to enable passage of blood from a region of high pressure, such as the left atrium, to a region of lower pressure, such as the right atrium. The dimensions of the shunt tube element 120 are chosen so as to be as small as possible while still allowing sufficiently rapid fluid flow without endangering blood coagulation induced by blood stasis or low-flow zones. Computational fluid dynamics methods can be used to appropriately shape the element so as to minimize low-flow zones and maximize laminar flow. The inside diameter of the shunt tube is preferably greater than 1 mm and less than 5 mm, but it will be understood that a wide range of shapes and diameters can be constructed that will effect the purpose of the present invention in a variety of patients and flow conditions within those patients. The shunt tube element 120 is preferably formed of either metallic or polymeric materials and may be coated and/or textured as mentioned above. Pyrolitic carbon coating, as is commonly used in implantable mechanical heart valves, can be used to increase the degree to which the surface is biologically inert. Examples of such commercially available materials include On-X{circle over (R)} Carbon, from Medical Carbon Research Institute, LLC, of Austin, Tex.

Also illustrated in FIG. 1 is a valve element 130, which as explained below is not necessarily included in all embodiments within the scope of the present invention and can be of a variety of forms. As illustrated a leaflet 131,132 can be used, either in a single piece or as a dual leaflet design as illustrated. In the embodiment shown in FIG. 1, each leaflet 131,132 is a flat plate that pivots to open and close the orifice of the shunt tube. A ball-and-socket design can be used as well. Another alternative design is the duckbill-type valve. The valve element can be formed using the same range or materials and coatings mentioned above for the shunt tube.

From the foregoing, it will be appreciated by those of skill in the art that the present invention is well adapted to percutaneous placement via femoral access, however, other implantation techniques such as surgical techniques using either an open chest procedure or those using minimally invasive techniques are also within the scope of the present invention.

The concepts of allowing pressure to be relieved in one area of the circulation by shunting to an area of lower pressure as disclosed herein may take many embodiments, all of which will be apparent to those of skill in the art upon review of the foregoing descriptions of the physiology and medicine involved, and the description of the embodiment of FIG. 1.

In accordance with the present invention, the device may or may not include the valve element 130, since in certain patients or to treat certain conditions a valve would add complexity while not providing necessary functionality. Similarly, depending upon the circumstances of use, the valve element 130 may be either passive (actuated by the force of blood) or active (actuated by some other portion of the device). In active valve embodiments, the valve element 130 may include electric or electromagnetic elements that can be selectively actuated to open and close the valve element 130 or, if the valve element is designed for gradual opening and closing, move the valve element 130 between a first position and a second position. In some embodiments, the valve will be chosen and designed so that it responds only upon certain conditions occurring within the heart, such as the following: absolute left atrial pressure, differential atrial pressure, other intra-cardiac pressures, other cardiovascular pressures, or other physiological conditions that might correlate to an exacerbated state of diastolic heart failure, such as blood oxygen saturation or pH. In such embodiments, response to any given pressure or differential pressure will imply that a portion of the implanted device is in fluid communication with the relevant pressure source or sources. These embodiments will provide robust and reliable functionality by being mechanical and operating with signal inputs. All shunts, whether they include a valve or not can be further enhanced by including a check-valve that will prevent backflow. Those of skill in the art will appreciate that it is typically desirable to prevent flow from the right heart to the left heart, and thus one or more check valves can be appropriately placed. A double-check valve allows blood pressure above a lower limit but below a higher limit to actuate the valve, thus in a preferred embodiment, shunting blood from the left side to the right side only during a period of diastole.

Figure 2:
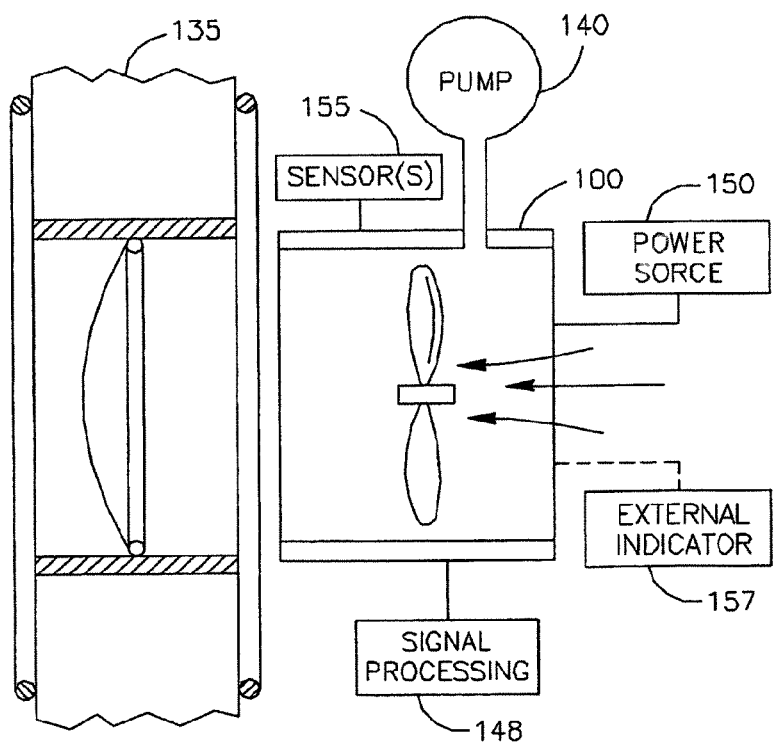
FIG. 2 is a side elevation view, in cross-section as shown by lines 2-2 in FIG. 1, illustrating the placement of the shunt shown in FIG. 1 in a septum, and showing diagrammatically the use of a pump to augment flow in certain embodiments.

Referring now to FIG. 2, another aspect of the devices of the present invention is that the shunt 100 may or may not be in fluid communication with a pump 140, such as either a surgically implanted pump that continuously moves a small amount of blood from one chamber or area to another, for example from the left ventricle chamber to the aorta for chronic reduction of LVEDP. Alternatively, the invention can include a catheter-based pump that continuously moves a small amount of blood from the LV chamber to the aorta for acute reduction of LVEDP. In certain preferred embodiments, the pump and valve will have a heart-synchronized actuated valve to allow specific regimens of left-to-right shunting to be applied. As seen in FIG. 2, after the shunt 100 is placed in a septum or other area, the pump 140 may be placed so as to direct fluid toward the shunt, the pump may be directly connected to the shunt, juxtaposed to the shunt, or displaced from the shunt but capable of directing flow in such a way as to effect more efficient pressure reduction.

FIG. 2 shows an implant similar to that of FIG. 1 that is placed surgically for the chronic reduction of LVEDP. This device includes a relatively small-sized pump 140, which can be similar to those used in Left-Ventricular Assist Devices (LVADs). Unlike the LVAD, however, the disclosed invention does not seek to significantly "support" the function of the left ventricle by pumping blood from the LV chamber to the body. Rather, it is intended only to "offload" the excessive pressure that builds through the diastolic phase of the cardiac cycle in some CBF patients. Whereas a normal LVEDP is in the range of 6-12 mmHg, patients with diastolic dysfunction heart failure (DDHF), end-diastolic pressure (EDP) in the left atrium (LA) and left ventricle (LV) can rise considerably above normal levels. Therefore the present invention encompasses a number of embodiments that are both capable of being either implanted during a surgical procedure or using a catheter (percutaneous). The shunt 100 allows blood to flow in the direction shown by the arrows so long as there is a lower pressure in the chamber or vessel adjoining the LV. In any embodiment, the methods and apparatus of the present invention reduce EDP, and in particular mitigate the most severe consequences of significantly increased EDP, such as pulmonary edema.

Thus, in preferred embodiments of the present invention the shunt is disposed in a wall between the chambers of a patient's heart, and most preferably, disposed in the atrial septum to permit blood to flow from the left ventricle when the pressure within the ventricle exceeds the pressure of the adjoining atrial chamber. In another particular embodiment, a sophisticated shunt apparatus implanted in the intra-atrial septum to allow intermittent and controlled blood flow from the left atrium to the right atrium (RA), thereby reducing LAEDP. Alternatively, the shunt might have its origin in locations other than the LA, such as the LV, and might have its output at locations other than the RA, such as the light ventricle (RV).

As explained above, although one class of embodiments of the present invention is designed to be purely mechanical and will have certain advantages, the present invention also encompasses additional embodiments wherein additional features such as internal signal processing unit 148 and an energy source 150, such as a battery, are included. In such embodiments, the shunts described above will include a valve apparatus that responds to conditions other than those occurring within the heart and/or has internal signal processing requiring an energy source. A device of this type responds according to programmed algorithms to all of the conditions mentioned above. The signal processing ability of devices in such embodiments enable adaptive approaches as well, in which the device response to conditions will change over time according to a pre-programmed adaptation algorithm. Such embodiments will include additional apparatus, such as a power source 150, sensors 155 and the like. The provision of implantable, programmable electrical devices that collect cardiac data and effect the operation of certain other elements of a device are well known in the field of cardiac pacing, for one example. In one particular embodiment, the actively controlled valve of the shunt as in senses and responds to electrical signals so as to act in synchronization with the cardiac cycle.

The pressure/flow/volume requirements of the various embodiments of the present invention will be determined using methodologies similar to those used to design a Left Ventricular Assist Device (LVAD) but with certain distinctly different flow requirements, rather than the intent of supporting systemic circulation requirements found in a LVAD. Thus, certain shunts made in accordance with the present invention can use designs and dimensions that would not be appropriate or adequate for an LVAD. Patients with heart failure dominated by systolic dysfunction exhibit contraction abnormalities, whereas those in diastolic dysfunction exhibit relaxation abnormalities. In most patients there is a mixed pathophysiology. Normal pulmonary venous pressure (PVP) necessary for the normal LV to adequately fill and pump is less than 12 mmHg. Patients with systolic dysfunction have larger LV volume to maintain SV and may need increased PVP to fill (mixed systolic diastolic dysfunction). Patients with diastolic dysfunction need increased PVP for the LV to fill and adequately pump.

The hemodynamic performance of the present invention, and thus the design of the shunt and its actuation, placement etc. will be determined by a variety of factors, for example, the following table is in the form of:

IF ({LAEDP} AND/OR {Mean LA P}) AND/OR ({ΔLAEDP-RAEDP} AND/OR {ΔMean LA P-Mean RA P}) THEN {ACTION}

In which LAEDP, Mean LA P, RAEDP and Mean RA P refer to minima, maxima or ranges for the respective pressures (please specify which in the table), and the AND/OR indicate that a logical operator or an NA (not applicable) should be entered

| Scenario | IF LAEDP | AND/OR | Mean LA P | AND/OR | Δ Atrial EDP | AND/OR | Δ mean atrial P | Then (Action) |
|---|---|---|---|---|---|---|---|---|
| Ex. | Exceeds 25 | Or | Exceeds 20 | NA | NA | NA | NA | Remove sufficient blood from the LA to reduce LA pressure by 5 mmHg |

Either passive or active devices may be linked to an external indicator 157, such as pendant worn by the patient, that displays the device status. Such an indicator enables the patient to notify a physician in the event of an activation of the implanted device that corresponds to the significantly exacerbated state heart failure. In this case, the device will be acting to prevent the occurrence of pulmonary edema during the time that the patient notifies a physician and then undergoes medical treatment to reduce the severity of the patient's condition.

Similarly, any embodiment of the present invention may be designed so that an external device can be used on occasion to either mechanically adjust (in the case of passive devices; for example, by magnetic coupling) and/or to reprogram (in the case of active devices) the functioning of the implanted device.

The methods mentioned above will prevent from excessive pressures to build up in the left ventricle and help restore wall stress in diastole and systole to normal values quickly thus helping the introduction of pharmacological agents as adjunct therapy or vice versa. This mode of therapy will be complementary to the current management of the patients and allow more controlled stabilization. It can be added as a component of cardiac pacemaker (dual or biventricular) and derive the power supply from the pacemaker battery.

Thus for example, a chronic device can be a preventive device where when pressures rise for some reason to dangerous levels the pump goes into action and helps to lower the pressure in the left ventricle, thereby preventing the acute development of dyspnea and pulmonary edema and assures that the LVDP are always at an optimal level of no more than 15 mmHg.

In other embodiments and for other indications, the present invention might move an extra volume of blood from the LV into the aorta. To do so, the pump 140 must be capable of moving blood from a chamber exhibiting 20 mmHg in diastole to 70 mmHg in the aorta. Another possible chamber where blood from the LA (throughout the cardiac cycle) or LV (only in diastole) can be directed to is the Right Atrium, and alternatively right ventricle. The benefit of directing blood from LA to RA is that the pressure differences are smaller and the blood can be moved in diastole and systole as well. Filling of the atria (R and L) during the systolic phase of the cardiac cycle determines the pressure in the atria at the onset of diastole and the opening of the valves.

Those of skill in the art will appreciate that there are a number of techniques for placement and locations for placement of shunts made in accordance with the present invention. For example, a surgically implanted passive shunt can be placed between the left ventricle and the right atrium for chronic reduction of LVEDP. Alternatively, a surgically implanted passive shunt can be placed between the left atrium and the right atrium for chronic reduction of LVEDP. For percutaneous placement, a catheter-based passive shunt can be inserted from the right atrium trans-septally into the left atrium for acute reduction of LVEDP. Another catheter-delivered embodiment is a passive shunt that is implanted from the right atrium trans-septally into the left atrium for chronic reduction of LVEDP.

Figure 3:
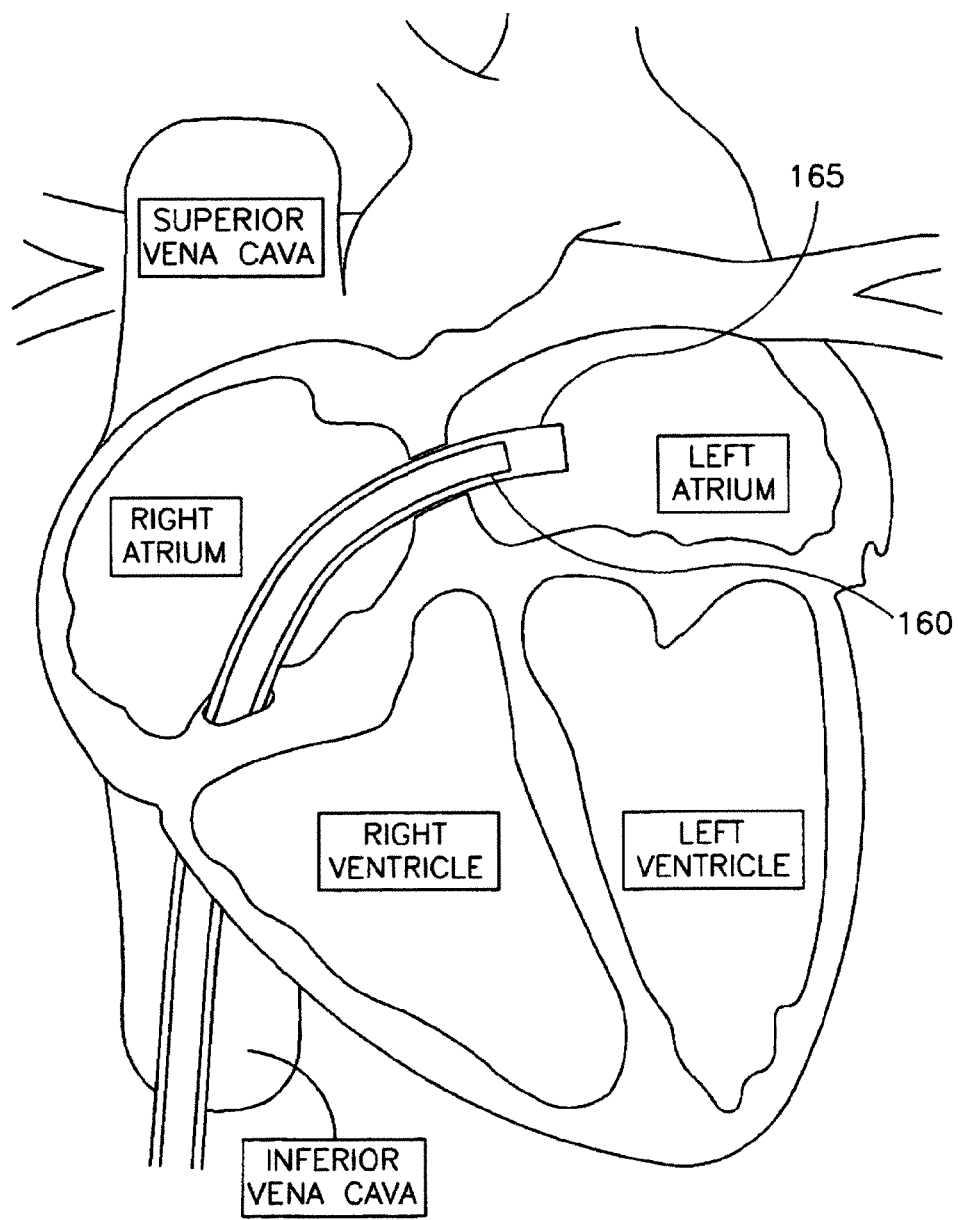
FIGS. 3-5 are a cross sectional view of a patient receiving a shunt made in accordance with the present invention via percutaneous placement.
Figure 4:
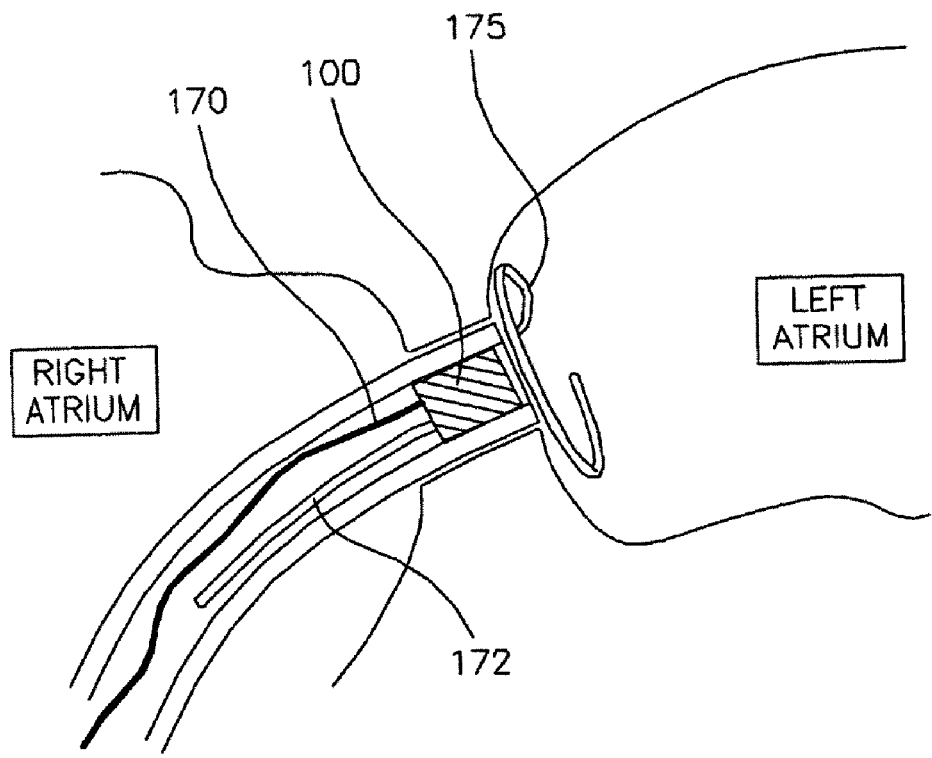
Figure 5:
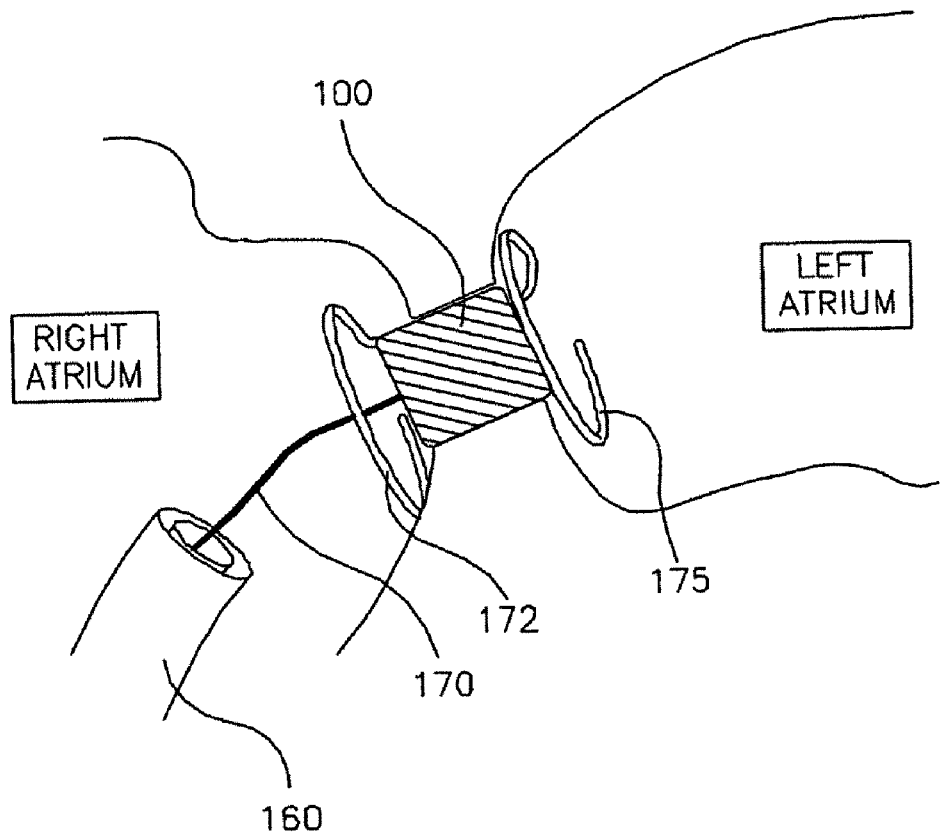

Although the present invention provides new and useful methods of treatment, the techniques of implanting shunts as described herein, is well known. For one example, in a preferred embodiment of the present invention, as illustrated in FIGS. 3-5, a transseptal needle set 160 is advanced toward the wall of the right atrial septum. Access has been made from the femoral vein with the system being advanced through the inferior vena cava and into the right atrium. Devices that allow such access and subsequent transseptal puncture are available from Cook Incorporated. For example, the procedure can be carried out using a stainless steel and obrturator set TSNC-18-71.0 for adults and TSNC-19-56.0 for pediatric patients. Once transseptal puncture has been achieved, a guidewire 170 is exchanged for the needle component in the commercially available device described above and then passed into the left atrium. The process of securing catheter access to the left atrium by way of a transseptal puncture is further described in the standard medical text Braunwald, Heart Disease, (Ch. 6, p. 186) which is incorporated herein by reference. After the transseptal sheath 165 is positioned in the left atrium, as described above, the placement of a shunt 100 made in accordance with the present invention is initiated. The following is a generalized sequence; the placement procedure will be done according to the typical methods of interventional cardiology as are well known to physicians trained in that subspecialty. The typical supporting apparatus found in the cardiac catheterization laboratory will be used, such as fluoroscopy for visualization and hemodynamic and ECG monitoring equipment to assess catheter position and patient vital signs.

The dilator and wire will be withdrawn from the sheath that now extends from the femoral vein access point in the patient's groin to the left atrium, traversing the femoral vein, the illiac vein, the inferior vena cava, the right atrium, and the atrial septum The delivery catheter will be passed through the sheath while under fluoroscopic visualization. Radiopaque markers are provided on this catheter as well as the sheath in order to locate specific points. The delivery catheter is carefully and slowly advanced so that the most distal portion of the left-atrial fixation wire is emitted from the distal opening of the catheter and into the chamber of the left atrium. The fixation wire is formed from a spring-like material and/or may be super-elastic of shape-memory alloy, so that as it leaves the constraint provided by the inner lumen of the delivery catheter, it reforms into its fully formed shape, which may circular or polygonal as previously disclosed. The assembly of the sheath and the delivery catheter are then slowly retracted en bloc so as to withdraw the fixation wire towards the atrial septum. The physician stops this retraction when it becomes apparent by fluoroscopic visualization as well as by tactile feedback that the fixation wire has become seated against the atrial septum. At that point, the sheath alone is retracted, uncovering the shunt and positioning it within the opening that has been created within the atrial septum. The sheath is then further retracted, allowing the right-atrial fixation wire to reform into its fully formed shape. The entire shunt assembly is then detached from the delivery catheter system The shunt is controlled within the delivery catheter by means of long controller wire that has independent translational control within the catheter lumen. This attachment is formed by any conventional method, e.g., a solder or adhesive or the like that will mechanically detach at a prescribed tension level, that level being exceeded by the physician at this point in the procedure by firmly retracting the controller wire.

Although certain embodiments have been set forth and described herein, numerous alterations, modifications, and adaptations of the concepts presented will be immediately apparent to those of skill in the art, and accordingly will lie within the scope of the present invention, as defined by the claims appended hereto.

What is claimed:

1. A device for decreasing blood pressure in the left atrium of a heart of a human with congestive heart failure, the device comprising:
    a shunt tube element configured for percutaneous placement across an atrial septum of the human with congestive heart failure so as to define a passageway between the right atrium and the left atrium through the atrial septum;
    a valve element disposed within the shunt tube element and configured to open to permit blood to flow from the left atrium to the right atrium through the shunt tube element only when the blood pressure in the left atrium exceeds the blood pressure in the right atrium; and
    a fixation element comprising first and second self-expanding end regions configured to retain the shunt tube element within the atrial septum,
    the device being configured such that the first self-expanding end region communicates with the left atrium and the second self-expanding end region communicates with the right atrium and reduces the blood pressure in the left atrium by transferring blood from the left atrium to the right atrium through the shunt tube element responsive to a predetermined differential atrial pressure.

2. The device of claim 1, wherein the first and second self-expanding end regions of the fixation element comprise first and second flanges.

3. The device of claim 2, wherein the first and second flanges are annular.

4. The device of claim 2, wherein the first and second flanges are configured to respectively engage first and second sides of the atrial septum.

5. The device of claim 1, wherein the valve element comprises at least two leaflets.

6. The device of claim 1, wherein the shunt tube element is cylindrical.

7. The device of claim 1, wherein the valve comprises a passive check-valve that allows blood flow only above a given threshold pressure.

8. The device of claim 1, wherein the fixation element surrounds and positions the shunt tube element.

9. The device of claim 1, wherein the valve element comprises a plurality of leaflets.

10. The device of claim 1, wherein the valve element comprises a leaflet.

* * * * *